United States Patent [19]

Yamamoto et al.

[11] Patent Number: 5,008,450
[45] Date of Patent: Apr. 16, 1991

[54] PROCESS FOR EXCHANGING DISPERSING MEDIUM OF TEREPHTHALIC ACID SLURRY

[75] Inventors: Ryoichi Yamamoto; Hiroshi Suzuki, both of Yamaguchi, Japan

[73] Assignee: Mitsui Petrochemical Industries, Ltd., Tokyo, Japan

[21] Appl. No.: 449,047

[22] Filed: Dec. 14, 1989

Related U.S. Application Data

[63] Continuation of Ser. No. 373,674, Jun. 28, 1989, abandoned, which is a continuation of Ser. No. 279,085, Dec. 2, 1988, abandoned.

[30] Foreign Application Priority Data

Dec. 17, 1987 [JP] Japan ................................ 62-319889

[51] Int. Cl.$^5$ ............................................. C07C 51/42
[52] U.S. Cl. ................................... 562/485; 562/414; 562/416; 562/417; 562/486
[58] Field of Search ............... 562/414, 416, 417, 485, 562/486

[56] References Cited

U.S. PATENT DOCUMENTS

| | | | |
|---|---|---|---|
| 3,873,609 | 3/1975 | Wu et al. | 562/485 X |
| 4,212,995 | 7/1980 | Shiraki | 562/485 |
| 4,357,475 | 11/1982 | Hanotier et al. | 562/414 |

FOREIGN PATENT DOCUMENTS

| | | |
|---|---|---|
| 3128474 | 6/1982 | Fed. Rep. of Germany . |
| 2478627 | 12/1982 | France . |
| 57-53431 | 3/1982 | Japan . |
| 2014985 | 9/1979 | United Kingdom . |

*Primary Examiner*—Jose G. Dees
*Assistant Examiner*—Vera C. Clarke
*Attorney, Agent, or Firm*—Sherman and Shalloway

[57] ABSTRACT

A process for exchanging a dispersing medium of a terephthalic acid slurry by introducing an aliphatic carboxylic acid slurry of terephthalic acid into a multi-stage column at the upper part thereof and introducing water at the lower part thereof to form an upflowing stream of water in the multi-stage column, while a sedimentation of terephthalic acid particles is effected, and withdrawing an aqueous aliphatic carboxylic acid solution from the upper part of the multi-stage column and an aqueous slurry of terephthalic acid from the lower part of the multi-stage column.

15 Claims, 1 Drawing Sheet

PROCESS FOR EXCHANGING DISPERSING MEDIUM OF TEREPHTHALIC ACID SLURRY

This application is a continuation of application Ser. No. 07/373,674 filed June 28, 1989, abandoned, which in turn is a continuation of Ser. No. 07/279,085 filed on Dec. 2, 1988 abandoned.

BACKGROUND OF THE INVENTION

1. Field of the Invention

The present invention relates to a process for exchanging a dispersing medium of an aliphatic carboxylic acid slurry of terephthalic acid. More specifically, it relates to a process for obtaining an aqueous slurry of terephthalic acid by exchanging, for example, the aliphatic acid, which is the dispersing medium in an aliphatic carboxylic acid slurry of terephthalic acid obtained by an oxidation of p-xylene in an aliphatic carboxylic acid dispersing medium, for water.

2. Description of the Related Art

Terephthalic acid is very useful as the starting material for polyester resin, etc., and is usually obtained by an oxidation of p-xylene in an aliphatic carboxylic acid solvent such as acetic acid, and as an aliphatic carboxylic acid slurry from the reaction apparatus. Terephthalic acid is insoluble in solvents such as water, alcohol, ether, chloroform, and acetic acid, and is sublimated without melting by heating to 300° C., and therefore, it is difficult to obtain a high purity terephthalic acid by utilizing conventional methods such as recrystallization or vacuum distillation from an aliphatic carboxylic acid slurry of terephthalic acid discharged from the reaction apparatus.

Accordingly, in the purification of terephthalic acid, a method has been employed in which crude crystals of terephthalic acid are separated from an aliphatic carboxylic acid slurry of terephthalic acid obtained from a reaction apparatus, the crude crystals are dispersed in water to obtain an aqueous slurry of terephthalic acid, and the aqueous slurry is hydrogenated by, for example, contact with hydrogen gas, to improve the solubility of the impurities and remove the impurities by dissolution into the solvent. In the steps of this purification method, since crude crystals of terephthalic acid are in the form of a fine powder and have a very low filtration efficiency, it is difficult to use a separation by filtration method, and thus a separation method such as centrifugation is usually adopted.

Nevertheless, to effectively separate crude crystals from the aliphatic carboxylic acid slurry of terephthalic acid by a centrifugation device, the centrifugation must be carried out at least two or three times, or more, and further, the crude crystals obtained by centrifugation must be dried to enable a reduction of the terephthalic acid crystals to a powder. Accordingly, a plurality of centrifugation devices, a drying device, and a storage for the particles are required, and therefore, the ratio of equipment cost to production cost becomes very high. Further, a problem arises in that the separation of crystals as described above is very cumbersome. Also, when producing an aqueous slurry by a dispersion of the terephthalic acid obtained as crude crystals in water, a problem arises in that the preparation of the aqueous slurry, such as the stirring of a mixture of the crude crystals and water at a high speed, is very cumbersome.

Japanese Unexamined Patent Publication (Kokai) No. 57-53431 discloses a washing process which is primarily characterized by washing crude terephthalic acid in a multi-stage washing column provided with partitioning plates having a plurality of holes arranged therein. This washing entails specifically a process in which terephthalic acid particles are washed when a terephthalic acid slurry in an aqueous mother liquor is introduced into the multi-stage washing column at the top thereof and water is introduced at the bottom thereof to effect a counter current contact therebetween, whereby terephthalic acid particles are sedimentated, and the dispersing medium constituting the terephthalic acid slurry and the washing solvent are both the same liquid, i.e., water, although some differences in the purity of both may exist.

SUMMARY OF THE INVENTION

Accordingly, the objects of the present invention are to eliminate the above-mentioned problems of the prior art and to provide a process for obtaining an aqueous slurry of terephthalic acid particles by exchanging an aliphatic carboxylic acid, which is the dispersing medium constituting an aliphatic carboxylic acid slurry of terephthalic acid, for water.

Another object of the present invention is to provide a process by which an aqueous slurry of terephthalic acid can be obtained by exchanging the aliphatic carboxylic acid constituting an aliphatic carboxylic acid slurry of terephthalic acid, by using a multi-stage column, and further, the aliphatic carboxylic acid such as acetic acid constituting the aliphatic carboxylic acid slurry can be recovered at a high concentration.

Other objects and advantages of the present invention will be apparent from the following description.

In accordance with the present invention, there is provided a process for exchanging a dispersing medium of a terephthalic acid slurry, which comprises introducing an aliphatic carboxylic acid slurry of terephthalic acid into a multi-stage column at the upper part thereof and introducing water at the lower part thereof to form an upflowing stream of water in the multi-stage column, while a sedimentation of terephthalic acid particles is effected, and withdrawing the aqueous aliphatic carboxylic acid solution from the upper part of the multi-stage column and an aqueous slurry of terephthalic acid from the lower part of the column.

BRIEF DESCRIPTION OF THE DRAWINGS

The present invention will be better understood from the description set forth below with reference to the accompanying drawing of FIG. 1, which schematically illustrates an example of the preparation steps of terephthalic acid including the step of the process for exchanging the dispersing medium of a terephthalic acid slurry according to the present invention.

DESCRIPTION OF THE PREFERRED EMBODIMENTS

Figure 1:
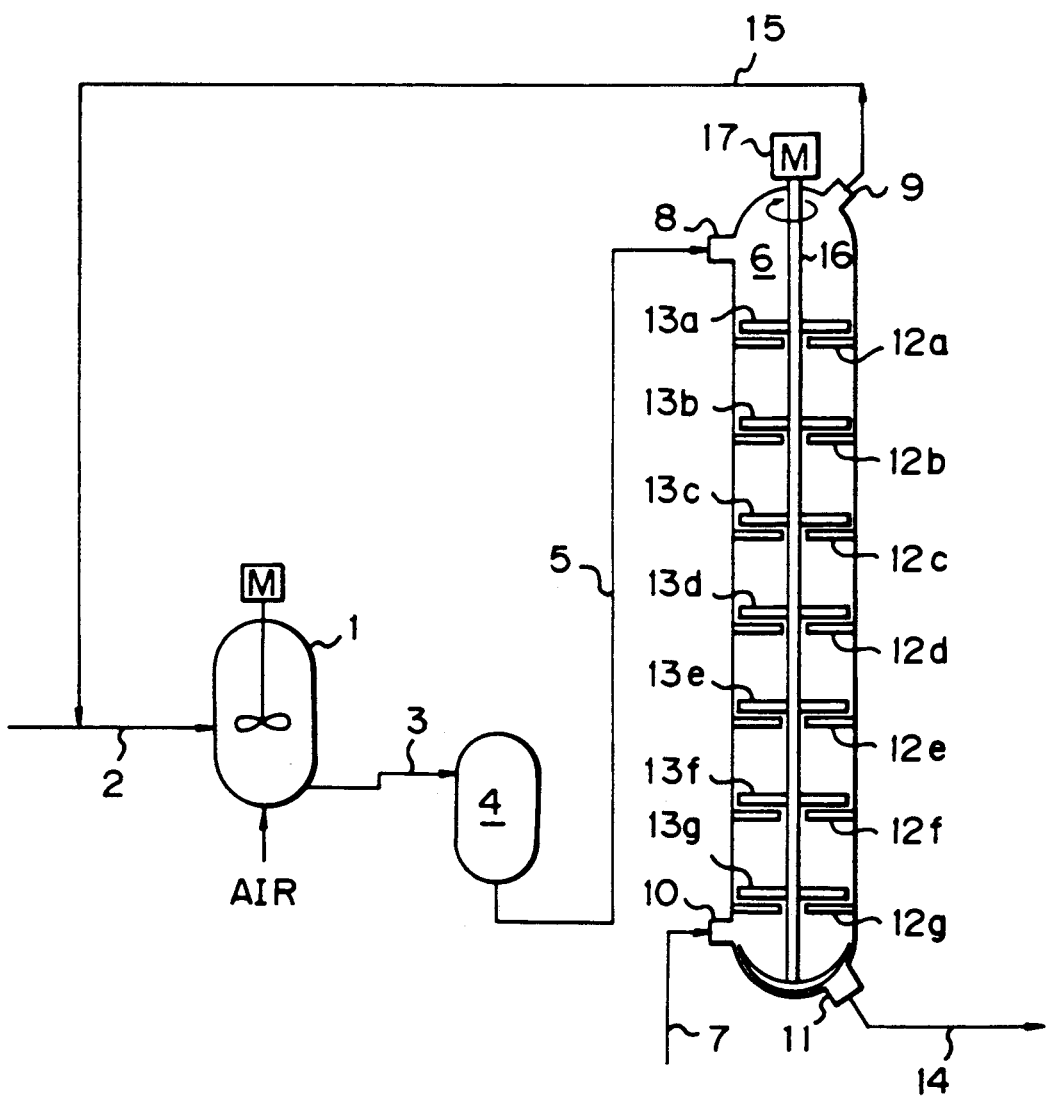

According to the process for exchanging the dispersing medium of a terephthalic acid slurry of the present invention, by using a multi-stage column, an aliphatic carboxylic acid slurry of terephthalic acid is introduced into the multi-stage column at the upper part thereof and water is introduced at the lower part thereof to form an upflowing stream in the multi-stage column and sedimentate terephthalic acid particles through the solution, whereby an aqueous slurry of terephthalic acid with a low aliphatic carboxylic acid content can be withdrawn from the bottom of the multi-stage column, and an aqueous slurry of terephthalic acid can be prepared easily without a separation of the terephthalic acid particles from the aliphatic carboxylic acid slurry of terephthalic acid.

Therefore, by employing the dispersing medium exchange process of the present invention, terephthalic acid can be handled while dispersed in a liquid, without separation by, for example, centrifugation, to obtain an aqueous slurry of terephthalic acid, and thus it is not necessary to carry out complicated operations such as a separation of terephthalic particles from the aliphatic carboxylic acid slurry followed by a dispersion in water, and accordingly, the amount of equipment required can be greatly reduced.

Further, an aqueous aliphatic carboxylic acid solution can be obtained from the upper part of the multi-stage column, and by removing water from the aqueous aliphatic carboxylic acid solution, the solvent obtained can be circulated as a part of the reaction solvent during the oxidation of p-xylene.

The process for exchanging the dispersing medium of a terephthalic acid slurry of the present invention is described in detail below.

FIG. 1 shows an example of the preparation steps for the production of terephthalic acid, including the step of exchanging the dispersing medium of a terephthalic acid slurry of the present invention.

In FIG. 1, p-xylene and an aliphatic carboxylic acid are introduced into a reaction apparatus 1 through a feed pipe 2. The reaction apparatus 1 is filled with catalysts of cobalt, manganese and a bromine compound, a heavy metal catalyst, or a noble catalyst containing oxygen.

Terephthalic acid can be produced in the presence of the above catalysts by bringing the p-xylene into contact with oxygen (usually air). This reaction is usually carried out by setting the reaction temperature to 100° C. to 240° C. and the reaction pressure to 5 to 60 atm. During the reaction, aldehydes, etc., can be optionally added as a reaction accelerator.

By thus oxidizing the p-xylene, an aliphatic carboxylic acid slurry of terephthalic acid is obtained, and such an aliphatic carboxylic acid slurry of terephthalic acid usually contains 5% to 50% by weight of particulate terephthalic acid, 50% to 95% by weight of aliphatic carboxylic acid, and 15% by weight or less of water.

In the production of terephthalic acid by an oxidation of p-xylene as described above, examples of the aliphatic carboxylic acid usable as the reaction solvent are acetic acid, proionic acid, n-butyric acid, isobutyric acid, n-valeric acid, trimethylacetic acid, caproic acid, and mixtures of these fatty acids with water. These can be used alone or in any combination thereof. Accordingly, the slurry of terephthalic acid to be used in the dispersing medium exchange process of the present invention is a slurry containing the above aliphatic carboxylic acid as the dispersing medium. The slurry to be used in the present invention can contain other components such as catalyst components, in addition to the above-mentioned aliphatic carboxylic acid. Particularly, since the oxidation reaction of p-xylene is preferably carried out in acetic acid, an acetic acid slurry of terephthalic acid is usually employed in the present invention.

In the present invention, although the aliphatic carboxylic acid slurry of terephthalic acid formed as described above can be directly introduced into the multi-stage column, preferably it is once introduced into a degassing vessel 4, to remove air, etc., contained in the slurry. Also, by thus introducing the slurry into the degassing vessel 4, an advantage is gained in that the amount of the slurry introduced into the multi-stage column can be more easily controlled.

The degassing vessel 4 and the multi-stage column 6 are connected through a pipe 5.

In the present invention, the aliphatic carboxylic acid slurry of terephthalic acid after introduction into the degassing vessel 4, or without introduction thereinto, is introduced into the upper part of the multi-stage column 6 through the pipe 5, simultaneously with the introduction of water at the lower part of the multi-stage column 6.

The multi-stage column 6 to be used in the present invention basically has the shape of a cylinder having a bottom, and provided at the upper part of the multi-stage column are an aliphatic carboxylic acid slurry introducing inlet 8 for introducing the aliphatic carboxylic acid slurry of terephthalic acid linked to the pipe 5 and an aqueous aliphatic carboxylic acid discharging outlet 9 for dispersing the aqueous aliphatic carboxylic acid solution. Further, at the bottom of the multi-stage column, a water introducing inlet 10 and an aqueous slurry discharging outlet 11 are provided. The aqueous aliphatic carboxylic acid solution discharging outlet 9 is usually provided above the aliphatic carboxylic acid slurry introducing inlet 8 to reduce the amount of terephthalic acid particles in the withdrawn aqueous aliphatic carboxylic acid solution. The aqueous slurry discharging outlet 11 is usually provided below the water introducing inlet 10.

At least one partitioning plate is arranged within the multi-stage column 6, which divides the multi-stage column into at least two vertical stages, so that terephthalic acid particles can be sedimentated from the upper part of the multi-stage column and water can flow from the lower part of the multi-stage column to the upper part thereof. In the present invention, the number of stages in the multi-stage column 6 can be set in accordance with the amount of aliphatic carboxylic acid slurry of terephthalic acid introduced, and the amount of aliphatic carboxylic acid which can be contained in the aqueous slurry of terephthalic acid withdrawn from the lower part of the multi-stage column. For example, when the aliphatic carboxylic acid concentration in the aqueous slurry of terephthalic acid is 10% by weight or less, a multi-stage column having 5 or more stages is usually employed. This partitioning plate allows a control of the falling speed of the terephthalic acid particles or the rising speed of the upflowing stream of water. In the Figure, the multi-stage column 6 is divided into 7 stages by 7 partitioning plates to 12a to 12g.

The respective partitioning plates can be set in accordance with the number of stages in the multi-stage column, and the speed of introduction of the aliphatic carboxylic acid slurry of terephthalic acid, but preferably are arranged at intervals of at least 10 cm. If the interval between the partitioning plates is less than 10 cm, the aliphatic carboxylic acid concentration in the aqueous slurry may become undesirably high.

Further, in the present invention, in addition to these partitioning plates, scrapers (scraping blades) 13a to 13g rotating at a low speed can be employed in combination. The scrapers 13a–13g are linked to a rotating shaft 16 rotated by a rotating means 17 at a speed of, for example, 0.5 to 20 rpm.

The partitioning plates and the scrapers may be provided with a number of fine passing holes through which terephthalic acid particles can pass, to control the speed of sedimentation of the terephthalic acid particles.

In the present invention, an aliphatic carboxylic acid slurry is introduced from the aliphatic carboxylic acid introducing inlet 8 provided at the upper part of the multi-stage column 6 as described above, and water is fed through the water introducing inlet 10 at the lower part of said multi-stage column 6. The water fed from the water introducing inlet 10 forms an upflowing stream inside the multi-stage column 6, and the terephthalic acid particles are sedimentated inside the multi-stage column 6. At this time, aliphatic carboxylic acid is also diffused downward in the multi-stage column 6, but the concentration of aliphatic carboxylic acid is lowered as the acid descends in the multi-stage column, and thus the concentration of aliphatic carboxylic acid at the lower part of the multi-stage column 6 is very low.

More specifically, the terephthalic acid particles have a specific gravity of about 1.5 g/cm$^3$, and are sedimentated naturally by the force of gravity. Particularly, in the present invention, terephthalic acid can be effectively sedimentated by using an aliphatic carboxylic acid slurry of terephthalic acid in which at least 90% by weight of the terephthalic acid particles have particle sizes of from 5 to 600 μm, preferably from 20 to 300 μm. Namely, if the aliphatic acid slurry contains a large amount of terephthalic acid particles with smaller particle sizes, the sedimentation of the terephthalic acid particles will be too slow, and thus the amount of the terephthalic acid particles in the aqueous aliphatic carboxylic acid solution recovered from the upper part of the multi-stage column will be increased. On the other hand, when a large amount of particles with larger particle sizes are contained, the sedimentation speed is too rapid, and thus the aliphatic carboxylic acid will contain sedimentated terephthalic acid particles and the aliphatic carboxylic acid concentration in the obtained aqueous slurry of terephthalic acid may become higher.

In the present invention, the amount of water for forming the upflowing stream of water is desirably about 0.01 to 5-fold relative to the weight of the terephthalic acid particles sedimentated in the multi-stage column. More specifically, since a multi-stage column having a large height/diameter (L/D) ratio is usually employed, it is theoretically possible to form an upflowing stream approximate to the piston flow by the elevation of a small amount of water, and due to this upflow, no aliphatic carboxylic acid should reach the lower part of multi-stage column. In practice, however, a small amount of aliphatic carboxylic acid will reach the lower part of the multi-stage column together with the sedimentated terephthalic acid particles, and therefore, the upflowing stream should contain a certain amount of water to prevent this phenomenon. If the amount of water is too high, however, the aqueous aliphatic carboxylic acid solution recovered from the aqueous aliphatic carboxylic acid solution discharging outlet 9 has a lower concentration, and therefore, the cost, of the operation for removing water when reusing the aqueous aliphatic carboxylic acid solution as the reaction solvent for terephthalic acid will be increased. Accordingly, preferably the weight of the terephthalic acid particles sedimentated in the multi-stage column and the weight of the water for forming the upflowing stream are as specified above.

The flow rate of the upflowing stream of water is desirably $2 \times 10^{-2}$ m/sec or lower in the vicinity of the aqueous aliphatic carboxylic acid solution discharging outlet 9, preferably $2 \times 10^{-4}$ to $5 \times 1 10^{-3}$ m/sec If the flow rate at this portion is too high, a large amount of the terephthalic acid particles is discharged from the aqueous aliphatic carboxylic acid discharging outlet 9. Further, in the process of the present invention, desirably the flow rate in the vicinity of the partitioning plate is $1 \times 10^{-2}$ m/sec. or lower, preferably $1 \times 10^{-4}$ or $3 \times 10^{-3}$ m/sec The flow rates at the respective portions can be controlled by, for example, varying the number or shape of the partitioning plates.

The sedimentation of the terephthalic acid particles in the multi-stage column 6 having an upflowing stream of water as described allows an aqueous slurry of terephthalic acid to be formed at the lower part of the multi-stage column. The aqueous slurry of terephthalic acid can be withdrawn from the aqueous slurry discharging outlet 11.

According to the dispersing medium exchange process of the present invention, the aliphatic carboxylic acid concentration in the aqueous slurry of terephthalic acid obtained is usually 10% by weight or less, and further, the aliphatic carboxylic acid concentration in the aqueous slurry can be made 1% by weight or less by suitably setting the number of stages in the multi-stage column, and the height of the multi-stage column.

The aqueous slurry of terephthalic acid obtained by the present invention is led to the subsequent step through a pipe 14. For example, the slurry can be introduced into a hydrogenation reaction apparatus for a selective hydrogenation of impurities in the aqueous slurry to improve the solubility of the impurities, followed by a removal thereof by dissolution, whereby a terephthalic acid having a very high purity can be produced.

The water slurry of terephthalic acid obtained by the present invention has a low aliphatic carboxylic acid concentration, and therefore, subsequent operations can be carried out without a specific separation of aliphatic carboxylic acid, and thus the loss of aliphatic carboxylic acid in the dispersing medium exchange is small. Also, even if the aqueous slurry is used as such in a later step, little corrosion of the apparatus used in the later step will occur.

On the other hand, aliphatic carboxylic acid diluted with water which has formed the upflowing stream can be obtained from the aqueous aliphatic carboxylic acid solution discharging outlet 9 at the upper part of the multi-stage column 6. This aqueous aliphatic carboxylic acid solution, after the water is removed therefrom, can be reused as a part of the reaction solvent during the production of terephthalic acid by an oxidation of p-xylene.

According to the dispersing medium exchange process of terephthalic acid slurry of the present invention, an aliphatic carboxylic acid slurry of terephthalic acid is introduced into the multi-stage column at the upper part thereof simultaneously with an introduction of water at the lower part thereof, to form an upflowing stream of water in the multi-stage column and thus effect sedimentation of terephthalic acid particles, whereby an aqueous slurry of terephthalic acid with very low aliphatic carboxylic acid content can be formed at the bottom of the multi-stage column, and by withdrawing this slurry, an aqueous slurry of terephthalic acid can be easily produced from an aliphatic carboxylic acid slurry.

Accordingly, by employing the dispersing medium exchange process of the present invention, without a separation of terephthalic acid powder by, for example, centrifugation, an aqueous slurry of terephthalic acid can be obtained, and thus the usual cumbersome operations and separation devices required for the separation of terephthalic acid particles can be omitted.

Further, according to the present invention, an aqueous slurry of terephthalic acid can be obtained directly from an aliphatic carboxylic acid slurry of terephthalic acid, and therefore, it is not necessary to separate the terephthalic acid particles or disperse the particles in water in the preparation of an aqueous slurry of terephthalic acid.

Also, an aqueous aliphatic carboxylic acid with a low water content can be obtained from the upper part of the multi-stage column, and if the water is removed from the aqueous carboxylic acid solution, the remaining solvent can be circulated as part of the reaction solvent during an oxidation of p-xylene.

EXAMPLES

The present invention will now be further illustrated by, but is by no means limited to, the following Examples.

Example 1

The reaction apparatus 1, degassing vessel 4, and multi-stage column 6 as shown in FIG. 1 were arranged as shown in FIG. 1.

Twenty partitioning plates were arranged at intervals of 20 cm in the multi-stage column, and 20 scrapers were also arranged therein. The scrapers were rotated at a speed of 1 rpm, and a stirring blade was provided at the tip end of the shaft for rotating the scrapers along the inner wall at the lower end of the multi-stage column.

From the pipe 2 of the above reaction apparatus 1 were introduced p-xylene and acetic acid, and terephthalic acid was produced by an air oxidation of p-xylene in an acetic acid solvent in the presence of cobalt acetate, manganese acetate, and tetrabromoethane catalysts.

The reaction conditions at this time were as follows:

| | |
|---|---|
| Reaction temperature | 190° C. |
| Reaction pressure (gauge) | 14 atm. |

The acetic acid slurry of terephthalic acid was withdrawn from the reaction apparatus 1 and introduced into the degassing vessel 4, to effect degassing for 5 minutes.

Next, the acetic acid slurry of terephthalic acid was introduced from the degassing vessel 4 into the multi-stage column 6 in an amount of 925 kg per hour, and 766 kg/hr of water was introduced from the lower part of the multi-stage column 6. The flow rate of the upflowing stream of water near the partitioning plates was $7 \times 10^{-4}$ m/sec.

The temperature of the water and the acetic acid slurry of terephthalic acid was 190° C. The acetic acid slurry contained 97% by weight of terephthalic acid particles within the particles size range of 20 to 300 μm.

The acetic acid slurry had the composition shown below:

| Composition of acetic acid slurry of terephthalic acid | |
|---|---|
| Terephthalic acid particles | 27.6 parts by weight |
| Acetic acid | 67.1 parts by weight |
| Water | 5.3 parts by weight. |

While introducing the acetic acid slurry of terephthalic acid and water as described above, an aqueous acetic acid solution was withdrawn in an amount of 713 kg per hour from the aqueous aliphatic carboxylic acid discharge outlet 9 provided at the upper part of the multi-stage column, and an aqueous slurry withdrawn in an amount of 978 kg/hr from the aqueous slurry discharging outlet 11 provided at the lower part. The flow rate of water at the tower top was $6 \times 10^{-3}$ m/sec The compositions of the obtained aqueous acetic acid solution and the aqueous slurry are shown below.

| Composition of aqueous acetic acid solution | |
|---|---|
| Terephthalic acid particles | 1.9 parts by weight |
| Acetic Acid | 87.0 parts by weight |
| Water | 11.1 parts by weight |

| Composition of aqueous slurry of terephthalic acid | |
|---|---|
| Terephthalic acid particles | 24.7 parts by weight |
| Acetic acid | 0.03 parts by weight |
| Water | 75.27 parts by weight |

As shown above, by employing the dispersing medium exchange process of the present invention, an aqueous slurry of terephthalic acid containing substantially no acetic acid was obtained by an exchange of the dispersing medium constituting the slurry without a separation of terephthalic acid particles from the acetic acid slurry of terephthalic acid. Further, an aqueous acetic acid solution with a low water content was recovered from the upper part of the multi-stage column, and the aqueous acetic acid solution, after the water was removed, was effectively reused as the reaction solvent during the oxidation reaction of p-xylene.

We claim:

1. A process for exchanging a dispersing medium of a terephthalic acid slurry, which comprises introducing an aliphatic carboxylic acid slurry of terephthalic acid into a multi-stage column at the upper part thereof and water at the lower part thereof to form an upflowing stream of water in the multi-stage column, while a sedimentation of terephthalic acid particles is effected, and withdrawing an aqueous aliphatic carboxylic acid solution from the upper part of the multi-stage column and an aqueous slurry of terephthalic acid from the lower part of the multi-stage column.

2. A process as claimed in claim 1, wherein at least 90% by weight of the terephthalic acid particles in the aliphatic carboxylic acid slurry have particle sizes of from 5 to 600 μm.

3. A process as claimed in claim 1, wherein the aliphatic carboxylic slurry of terephthalic acid contains 5% to 50% by weight of particulate terephthalic acid, 50% to 95% by weight of aliphatic carboxylic acid, and 15% by weight or less of water.

4. A process as claimed in claim 1, wherein the aliphatic carboxylic acid is at least one acid selected from the group consisting of acetic acid, propionic acid, n-butyric acid isobutyric acid, n-valeric acid, trimethylacetic acid and caproic acid.

5. A process as claimed in claim 1, wherein the amount of the upflowing water is 0.01 to 5-fold relative to the weight of the terephthalic acid particles sedimentated in the multi-stage column.

6. The process of claim 1 which further comprises separating the aliphatic carboxylic acid from the aqueous aliphatic carboxylic acid solution and recycling the separated acid to a step of forming the aliphatic carboxylic acid slurry of terephthalic acid.

7. The process of claim 1 wherein said aliphatic carboxylic acid comprises acetic acid.

8. The process of claim 1 wherein the aqueous aliphatic carboxylic acid solution is withdrawn from the upper portion of said column at a higher point that the point of introduction of said slurry while the aqueous slurry of terephthalic acid is withdrawn from the lower portion of the column at a point below the point of introducing water into the column.

9. The process of claim 1 wherein a plurality of partitioning plates are arranged within the multi-stage column to provide a plurality of stages therein, said partitioning plates being arranged at intervals of at least 10 centimeters from each other.

10. The process of claim 3 wherein at least 90% by weight of the terephathalic acid particles have particle sizes of from 5 to 600 $\mu$m.

11. The process of claim 9 wherein the amount of water forming said upflowing water stream is 0.01 to 5-fold relative to the weight of the sedimenting terephthalic acid particles in the column.

12. The process of claim 11 whrein the flow rate of the upflowing stream of water in the upper portion of the column is from about $2 \times 10^{-4}$ to $5 \times 10^{-3}$ m/sec.

13. The process of claim 12 wherein the flow rate of the upflowing streamof water in the vicinity of said partitioning plates is from about $1 \times 10^{-4}$ to $3 \times 10^{-3}$ m/sec.

14. The process of claim 1 wherein said aqueous slurry of terephthalic acid withdrawn from said column contains less than 1% by weight of said aliphatic carboxylic acid.

15. The process of claim 1 which further comprises a step of degassing the terephthalic acid slurry to remove air present therein prior to introducing the slurry into said column.

* * * * *